United States Patent
Fukuma et al.

(10) Patent No.: US 8,970,848 B2
(45) Date of Patent: Mar. 3, 2015

(54) OPTICAL IMAGE MEASUREMENT APPARATUS

(75) Inventors: Yasufumi Fukuma, Tokyo (JP); Masahiro Akiba, Tokyo (JP); Kinpui Chan, Oakland, NJ (US)

(73) Assignee: Kabushiki Kaisha Topcon, Tokyo (JP)

( * ) Notice: Subject to any disclaimer, the term of this patent is extended or adjusted under 35 U.S.C. 154(b) by 531 days.

(21) Appl. No.: 13/375,160

(22) PCT Filed: May 20, 2010

(86) PCT No.: PCT/JP2010/003407
§ 371 (c)(1), (2), (4) Date: Jan. 11, 2012

(87) PCT Pub. No.: WO2010/140313
PCT Pub. Date: Dec. 9, 2010

(65) Prior Publication Data
US 2012/0113431 A1    May 10, 2012

(30) Foreign Application Priority Data
Jun. 3, 2009   (JP) .................................. 2009-134516

(51) Int. Cl.
*G01B 11/02*   (2006.01)
*G01N 21/47*   (2006.01)
(Continued)

(52) U.S. Cl.
CPC ............ *G01N 21/4795* (2013.01); *A61B 3/102* (2013.01); *A61B 3/1225* (2013.01); *G01N 2021/1787* (2013.01)
USPC .......................................................... 356/497

(58) Field of Classification Search
USPC ....................................................... 356/456
See application file for complete search history.

(56) References Cited

U.S. PATENT DOCUMENTS 5,371,588 A * 12/1994 Davis et al. .................... 356/489
7,492,466 B2 * 2/2009 Chan et al. ..................... 356/497
(Continued)

FOREIGN PATENT DOCUMENTS

JP    07-092656 A    7/1995
JP    2004-251838 A   9/2004
(Continued)

OTHER PUBLICATIONS

Simultaneous SLO/OCT imaging of the human retina with axial eye motion correction, Optics Express, vol. 15, No. 25 (2007). Hitzenberger et al.*

(Continued)

*Primary Examiner* — Tarifur Chowdhury
*Assistant Examiner* — Jonathon Cook
(74) *Attorney, Agent, or Firm* — Pearne & Gordon LLP

(57) ABSTRACT

A motion detector 220 calculates the Doppler frequency shift amount based on the movement velocity of an eye E. A drive controller 230 calculates the modulation frequency of the intensity of output light M based on this Doppler frequency shift amount. A light source unit 201 outputs the light M in which the intensity is modulated with this modulation frequency. The light M is divided into a signal light S and a reference light R. Interference light L is generated by superimposing the signal light S passing through the eye E and the reference light R. Two polarized components of the interference light L have a phase difference of 180°, resulting from a quarter-wave plate 207. The polarized components L1, L2 which are divided by a polarization beam splitter 211 are detected by CCD 212, 213. A computer 250 forms a tomographical image based on these detection results.

4 Claims, 10 Drawing Sheets

(51) Int. Cl.
*A61B 3/10* (2006.01)
*A61B 3/12* (2006.01)
*G01N 21/17* (2006.01)

(56) References Cited

U.S. PATENT DOCUMENTS

| | | | |
|---|---|---|---|
| 2006/0077395 A1 | 4/2006 | Chan et al. | |
| 2006/0100528 A1 | 5/2006 | Chan et al. | |
| 2008/0208022 A1 | 8/2008 | Kruger et al. | |
| 2011/0105874 A1* | 5/2011 | Feddes et al. | 600/372 |
| 2011/0157552 A1* | 6/2011 | Bublitz et al. | 351/209 |

FOREIGN PATENT DOCUMENTS

| | | |
|---|---|---|
| JP | 2006-112864 A | 4/2006 |
| JP | 2006-153838 A | 6/2006 |
| JP | 2008-039651 A | 2/2008 |
| JP | 2008-545500 A | 12/2008 |
| JP | 2009-022502 A | 2/2009 |

OTHER PUBLICATIONS

Moneron G. et al. Stroboscopic ultrahigh-resolution full-field optical coherence tomography. In: Optics Letters, vol. 30, No. 11; Jun. 1, 2005; pp. 1351-1353.

International Search Report for PCT/JP2010/003407; mail date Jul. 20, 2010.

* cited by examiner

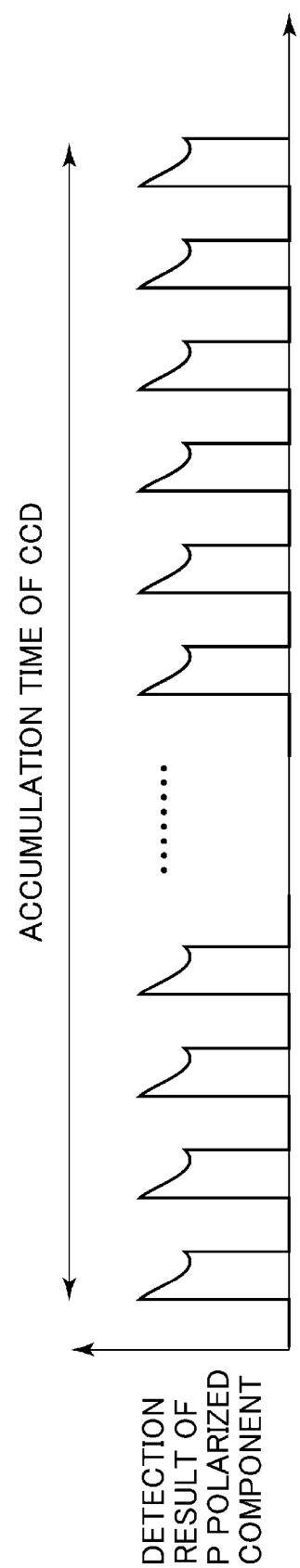

OPTICAL IMAGE MEASUREMENT APPARATUS

TECHNICAL FIELD

The present invention relates to an optical image measurement apparatus that forms images of measured objects by using optical coherence tomography.

BACKGROUND ART

In recent years, attention has been paid to optical image measurement technologies that form images of the surface and inner sections of measured objects using light. Optical image measurement technologies are not invasive to the human body, unlike radiographic imaging, making them promising particularly in the medical field. Among these technologies, significant progress is being achieved in the fields of ophthalmology, dentistry, dermatology, etc. Moreover, technologies are also being applied in the field of biology and engineering.

Optical coherence tomography (OCT) is a representative method of optical image measurement technologies. With this method, it is possible to measure at high resolution and highly sensitivity due to the use of interferometers. Moreover, because weak wideband light is used for illumination, this method is advantageous in that it provides high safety to the human body, etc.

Examples of apparatuses using OCT (OCT apparatus) include the apparatus described in Patent Document 1. This OCT apparatus generates interference light by superimposing light passing through the cornea (signal light) and light passing through a reference object (reference light) to form an image of the cornea, based on the detection results of this interference light. Accordingly, the obtained image is an image of a cross-section that is substantially perpendicular to the propagating direction of signal light. This method is referred to as a full-field type or an en-face type. This type of OCT apparatus is characterized by being able to obtain high-powered and high resolution images, compared to other types, and for example, it can be applied to observe microstructures (cells, etc.) of the cornea.

Other types of OCT apparatuses include swept source OCT, Fourier domain OCT, polarization-sensitive OCT, Doppler OCT, etc.

When measuring moving measured objects such as a living eye with OCT apparatuses, a phenomenon, namely fringe washout, may occur (for example, refer to Patent Document 2). Fringe washout is a phenomenon in which the detection sensitivity of the interference light decreases as a result of the effect of movement of measured objects (that is, the interference fringes become unclear), causing image definition to decrease.

An explanation is provided regarding fringe washout which occurs with full-field type OCT apparatuses. When measured objects move in the optical axial direction of the signal light, a Doppler frequency shift occurs with the signal light. Interfering components $I_{interference}$ of interference signals generated as the signal light interferes with the reference light that is reflected on a reference mirror (rest state) are expressed in the following formula in which amplitude is modulated.

[Formula 1]

$$I_{interference} = \sqrt{I_s I_r} \sin(2\pi f_{Doppl} t + \phi) \quad (1)$$

Here, if the optical refraction index of a measured object is n, the speed of the measured object in the optical axial direction is v, and the wavelength of the signal light is $\lambda$, the amount of Doppler frequency shift (Doppler frequency shift amount) is expressed as $f_{Doppl} = 2nv/\lambda$. Moreover, in Formula (1), $I_s$ is the intensity of the signal light, $I_r$ is the intensity of the reference light, and $\phi$ is the initial phase difference.

When the interfering components in Formula (1) are detected with an electric charge storage-type light detecting device such as a CCD, these interfering components are integrated within a storage time (may also be referred to as exposure time) of the device and can be represented by the following formula. Note that < > is a integration sign.

[Formula 2]

$$I_{interference} = \langle \sqrt{I_s I_r} \sin(2\pi f_{Doppl} t + \phi) \rangle \quad (2)$$

As is clear from Formula (2), the term expressed in the sine function resulting from the integration effect of the device is averaged. This is the fringe washout phenomenon. This type of decrease in the detection sensitivity attributable to movement of measured objects is described in, for example, Non-Patent Document 1. This document describes that the larger the movement velocity of the signal light in the optical axial direction is, the weaker the interference signals are (that is, the detection sensitivity decreases).

PRIOR ART DOCUMENTS

Patent Documents

[Patent Document 1] Japanese Unexamined Patent Application Publication 2009-22502

[Patent Document 1] Japanese Unexamined Patent Application Publication 2008-39651

Non-Patent Document

[Non-Patent Document 1] "Stroboscopic ultrahigh-resolution full-field optical coherence tomography", G. Moneron, A. C. Boccara, and A. Dubois, OPTICS LETTERS, Vol. 30, No. 11, Jun. 1, 2005

SUMMARY OF THE INVENTION

Problems to be Solved by the Invention

With conventional optical image measurement apparatuses that use optical coherence tomography, it was difficult to obtain clear images of moving measured objects, resulting from the effect of the abovementioned fringe washout. In particular, with the living eye, movement attributable to blood flow (pulse beats) and relatively fast and irregular movement resulting from accommodative micromovement, etc., occur, making it extremely difficult to obtain clear images.

The present invention was invented in order to solve the above problems, with the object of providing an optical image measurement apparatus that can obtain clear images even if measured objects are moving.

Means for Solving the Problem

In order to solve the above problem, a first aspect of the invention is an optical image measurement apparatus comprising: an optical system that divides light output from a light source into a signal light and a reference light, irradiates a measured object with said signal light, generates interference light by superimposing said signal light passing through said measured object and said reference light passing through a reference light path, and detects the interference light; a modulating section that modulates the intensity of light output from said light source at a frequency corresponding to the movement velocity of said measured object in the irradiation direction of said signal light with respect to said measured object; and a forming section that forms an image of said measured object based on the detection result of said interference light generated by said optical system, based on the light in which said intensity is modulated.

Moreover, a second aspect of the invention is the optical image measurement apparatus according to the first aspect, wherein said modulating section includes a measurement section that measures the state of motion of said measured object in said irradiation direction and modulates the intensity of said light at a frequency based on the measurement result.

Moreover, a third aspect of the invention is the optical image measurement apparatus according to the second aspect, wherein said measurement section includes a measurement light source; a measurement optical system that irradiates said measured object along said irradiation direction with measured light output from said measurement light source; and a light receiving section that receives reflected light from said measured object of the irradiated measurement light, and calculates the Doppler frequency shift amount, as said state of motion, corresponding to the movement velocity of said measured object in said irradiation direction based on the light receiving result from said light receiving section, and said modulating section modulates the intensity of said light at a frequency based on said Doppler frequency shift amount.

Moreover, a fourth aspect of the invention is the optical image measurement apparatus according to the third aspect, wherein said measurement optical system includes a half-mirror that reflects some of the measurement light output from said measurement light source and transmits some of the light, said light receiving section receives interference light between the reflected light from said measured object resulting from said some of measurement light transmitted from said half-mirror and said some of measurement light reflected to said half-mirror, and said measurement section calculates the frequency of the received interference light as said Doppler frequency shift amount.

Moreover, a fifth aspect of the invention is the optical image measurement apparatus according to the third aspect, wherein said measurement optical system comprises a measurement interferometer that includes a measurement light dividing section that divides the measurement light output from said measurement light source into two; and a reflecting mirror that reflects one of the two divided measurement lights, and generates interference light between the reflected light from said reflecting mirror of said one measurement light and the reflected light from said measured object of the other measurement light, said light receiving section receives interference light that is generated from said measurement interferometer, and said measurement section calculates the frequency of said received interference light as said Doppler frequency shift amount.

Moreover, a sixth aspect of the invention is the optical image measurement apparatus according to the second aspect, wherein said measurement section includes: a change section that changes the frequency of light that passes through said reference light path by a predetermined frequency; a measurement light source; a measurement optical system that divides the measurement light output from said measurement light source into a first measurement light and a second measurement light, irradiates said measured object with said first measurement light, and generates measurement interference light by superimposing said first measurement light passing through said measured object and said second measurement light passing through said reference light path and in which the frequency is changed by said predetermined frequency; and a light receiving section that receives said measurement interference light, and said measurement section calculates the frequency of said measurement interference light based on the light receiving result by said light receiving section, and calculates the Doppler frequency shift amount corresponding to the movement velocity of said measured object in said irradiation direction based on the frequency of said measurement interference light and said predetermined frequency, as said state of motion, and said modulating section modulates the intensity of said light at a frequency based on said Doppler frequency shift amount.

Moreover, a seventh aspect of the invention is the optical image measurement apparatus according to the third aspect, wherein said modulating section modulates the intensity of said light at the frequency obtained by multiplying the ratio of the wavelength of the light output from said light source and the wavelength of said measurement light by said Doppler frequency shift amount.

Moreover, an eighth aspect of the invention is the optical image measurement apparatus according to the sixth aspect, wherein said modulating section modulates the intensity of said light at the frequency obtained by multiplying the ratio of the wavelength of the light output from said light source and the wavelength of said measurement light by said Doppler frequency shift amount.

Moreover, a ninth aspect of the invention is an optical image measurement apparatus comprising: an optical system that divides light output from a light source into a signal light and a reference light, irradiates a measured object with said signal light, generates interference light by superimposing said signal light passing through said measured object and said reference light passing through a reference light path, and detects the interference light; a change section that changes the frequency of light passing through said reference light path; a controller that causes said change section to change the frequency based on the movement velocity of said measured object in the irradiation direction of said signal light with respect to said measured object; and a forming section that forms an image of said measured object based on the detection results of said interference light generated by said optical system, based on said signal light passing through said measured object and the reference light in which the frequency is changed by said controller.

Moreover, a tenth aspect of the invention is the optical image measurement apparatus according to the ninth aspect, wherein said controller includes a measurement section that measures the state of motion of said measured object in said irradiation direction, and causes said change section to change the frequency based on the measurement result.

Moreover, an eleventh aspect of the invention is the optical image measurement apparatus according to the tenth aspect, wherein said measurement section includes: a measurement light source; a measurement optical system that divides the measurement light output from said measurement light source into a first measurement light and a second measurement light, irradiates said measured object with said first measurement light, and generates measurement interference light by superimposing said first measurement light passing through said measured object and said second measurement light passing through said reference light path and in which the frequency is changed by said predetermined frequency;

and a light receiving section that receives said measurement interference light, and said measurement section calculates the frequency of said measurement interference light based on the light receiving results by said light receiving section, and calculates the Doppler frequency shift amount corresponding to the movement velocity of said measured object in said irradiation direction based on the frequency of said measurement interference light and the change amount of the frequency by said change section, as said state of motion, and said controller causes said change section to change the frequency by a new change amount based on said Doppler frequency shift amount.

Moreover, a twelfth of the invention is the optical image measurement apparatus according to the second aspect, wherein said optical system includes an optical path length change section that changes the optical path length of said reference light, and comprises an optical path length controller that calculates the displacement of said measured object in said irradiation direction based on said state of motion measured by said measurement section, and changes said optical path length by said displacement by controlling said optical path length change section.

Moreover, a thirteenth aspect of the invention is the optical image measurement apparatus according to the tenth aspect, wherein said optical system includes an optical path length change section that changes the optical path length of said reference light, and comprises an optical path length controller that calculates the displacement of said measured object in said irradiation direction based on said state of motion measured by said measurement section, and changes said optical path length by said displacement by controlling said optical path length change section.

Moreover, a fourteenth aspect of the invention is the optical image measurement apparatus according to the first aspect, wherein said optical system includes: a quarter-wave plate that is provided on one of the optical paths among said signal light and said reference light and that provides an optical path difference equal to one-half the wavelength between two polarized components of said one light; a division section that divides said interference light into said two polarized components; and two detectors that detect said two divided polarized components and outputs electrical signals, and said forming section forms an image of said measured object based on said two electrical signals based on the two polarized components detected substantially at the same time by said two detectors.

Moreover, a fifteenth aspect of the invention is the optical image measurement apparatus according to the ninth aspect, wherein said optical system includes: a quarter-wave plate that is provided on one of the optical paths among said signal light and said reference light and that provides an optical path difference equal to one-half the wavelength between two polarized components of said one light; a division section that divides said interference light into said two polarized components; and two detectors that detect said two divided polarized components and outputs electrical signals, and said forming section forms an image of said measured object based on said two electrical signals based on the two polarized components detected substantially at the same time by said two detectors.

Effect of the Invention

The optical image measurement apparatus according to the present invention is configured so as to modulate the intensity of output light from a light source at a frequency corresponding to the movement velocity of a measured object and form images of the measured object based on the detection results of the interference light based on this output light; thereby, making it possible to cause the modulation frequency of the intensity of the output light to track the Doppler frequency shift amount based on the movement velocity of the measured object and carry out measurement. Accordingly, even if the measured object is moving, it is possible to obtain clear images.

Moreover, the optical image measurement apparatus according to the present invention is configured so as to change the frequency of the reference light based on the movement velocity of the measured object and form images of the measured object based on the detection results of the interference light based on this reference light and the signal light; thereby, making it possible to carry out measurement while changing the frequency of the reference light according to the Doppler frequency shift amount based on the movement velocity of the measured object. Accordingly, even if the measured object is moving, it is possible to obtain clear images.

BRIEF DESCRIPTION OF THE DRAWINGS

FIG. 6C is a drawing for explaining an example of an interference signal obtained by an embodiment of an optical image measurement apparatus according to the invention.

MODE FOR IMPLEMENTING THE INVENTION

Explanations are provided with regard to embodiments of the optical image measurement apparatus according to the present invention. Below, a measurement principle according to the present invention is first explained, and subsequently, an explanation is provided regarding an optical image measurement apparatus to which this measurement principle is applied.

[Measurement Principle]

The measurement principle according to the present invention is explained with reference to FIG. 1. This optical image measurement apparatus 1000 improves the effect of fringe washout by carrying out intensity modulation on the light output from a light source.

The following measurement is generally carried out for optical coherence tomography. Output light M from a light source 1001 is divided into a reference light R towards a reference mirror 1003 and a signal light S towards a measured object 1006, by a beam splitter 1002. The reference light R returns to the beam splitter 1002 after it is reflected by the reference mirror 1003. The signal light S returns to the beam splitter 1002 after it is reflected and scattered on the surface and the inner sections of the measured object 1006. The beam splitter 1002 superimposes the signal light S and the reference light R in order to create interference. Interference light L generated accordingly is detected by a light detecting device 1004 (CCD, etc.). An image (tomographical images and 3-dimensional images) of the inner sections and the surface of the measured object 1006 is formed by analyzing this detection result (interference signals). This processing is performed by a computer (forming section), not shown in the figures.

Figure 1:
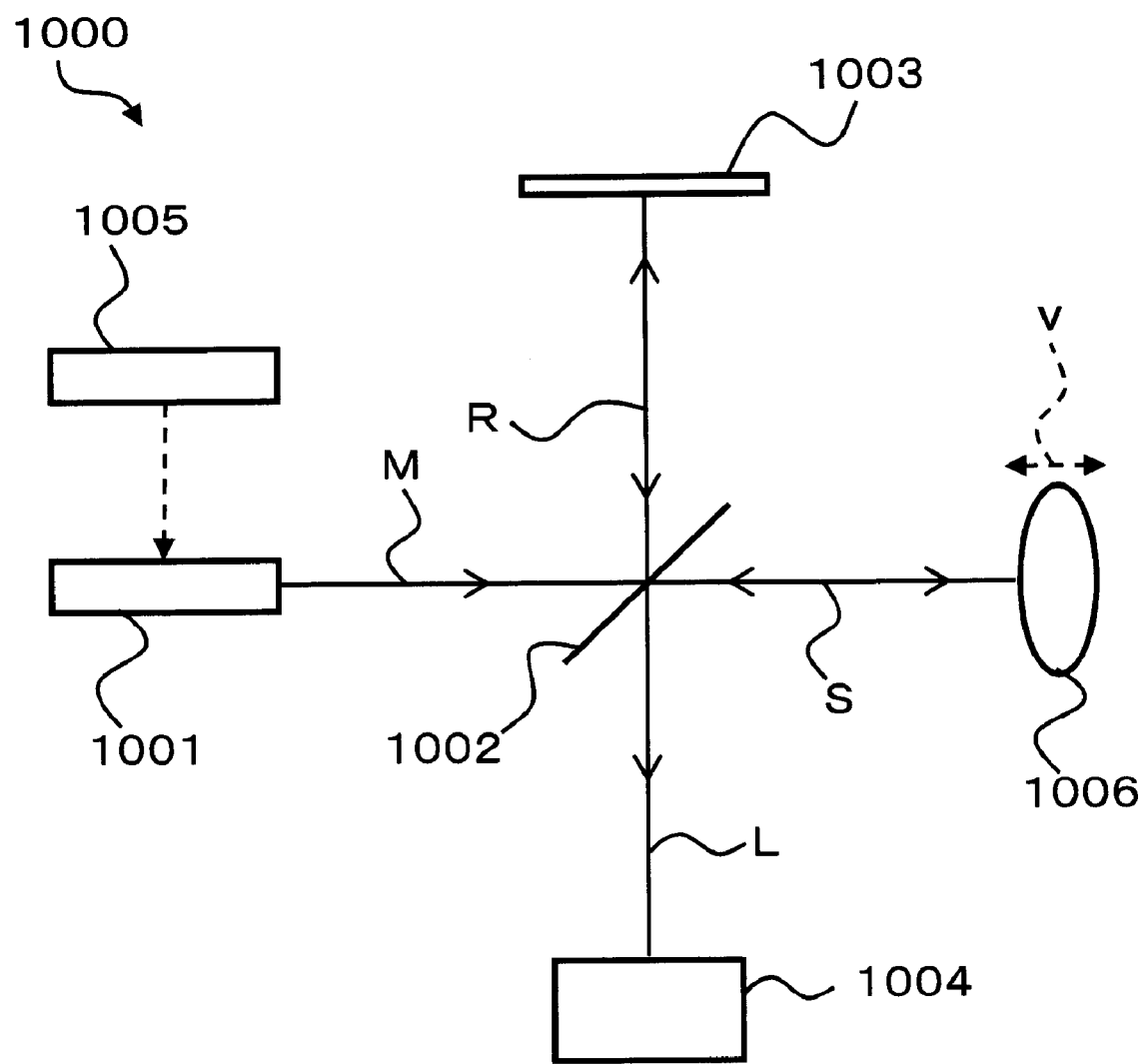
FIG. 1 is a schematic drawing for explaining the measurement principle of an optical image measurement apparatus according to the invention.

As shown in FIG. 1, if the measured object 1006 is moving in the optical axial direction (propagating direction) of the signal light S at a speed of v, clear images cannot be obtained with conventional measurement methods, as a result of fringe washout.

In contrast to this, with the present invention, by modulating the intensity of the output light M at a predefined frequency with an intensity modulator 1005 (modulating section), the effect of fringe washout is improved. This principle is explained below.

Interfering components of the interference signals output from the light detecting device 1004 are expressed in the following formula.

[Formula 3]

$$\langle \sqrt{I_s I_r} \sin(2\pi f_{mod} t + \phi')\sin(2\pi f_{Doppl} t + \phi) \rangle = \tfrac{1}{2}\sqrt{I_s I_r} \langle \cos[2\pi(f_{mod}+f_{Doppl})t+\Delta\phi'] + \cos[2\pi(f_{mod}-f_{Doppl})t+\Delta\phi] \rangle \quad (3)$$

Here, $I_s$ is the intensity of the signal light S and $I_r$ is the intensity of the reference light R. Moreover, $f_{mod}$ is the modulation frequency of the intensity of the output light M, resulting from the intensity modulator 1005. Furthermore, $f_{Doppl}$ is the Doppler frequency shift amount of the signal light S, resulting from movement of the measured object 1006. Furthermore, $\Delta\phi$ and $\Delta\phi'$ are phase differences based on the initial phase differences $\phi$, $\phi'$.

If the sum of the modulation frequency and the Doppler frequency shift amount $(f_{mod}+f_{Doppl})$ is sufficiently higher than the response frequency (reciprocal number of the storage time) of the light detecting device 1004, the first term on the right side of Formula (3) is averaged resulting from the cumulative effect and is considered to be zero. In the subsequent configuration example, the sum of the modulation frequency and the Doppler frequency shift amount is sufficiently higher than the response frequency of the light detecting device 1004 and the first term on the right side of Formula (3) is set so as to be averaged.

In contrast, if the difference between the modulation frequency and the Doppler frequency shift amount $(f_{mod}-f_{Doppl})$ is set so as to be lower than the response frequency of the light detecting device 1004, the second term on the right side of Formula (3) is detected as interfering components without being averaged.

Therefore, by setting it such that the difference between the modulation frequency and the Doppler frequency shift amount is lower than the response frequency, the interfering components as shown in the following formula are detected.

[Formula 1]

$$\langle \sqrt{I_s I_r} \sin(2\pi f_{mod} t + \phi')\sin(2\pi f_{Doppl} t + \phi) \rangle = \tfrac{1}{2}\sqrt{I_s I_r} \langle \cos[2\pi(f_{mod}-f_{Doppl})t+\Delta\phi] \rangle \quad (4)$$

In this way, the effect of fringe washout with respect to the interfering components is improved. Furthermore, by setting the modulation frequency and the Doppler frequency shift amount so as to be equal $(f_{mod}=f_{Doppl})$, the interfering components as shown in the following formula can be obtained, making it possible to eliminate the effect of fringe washout.

[Formula 2]

$$\langle \sqrt{I_s I_r} \sin(2\pi f_{mod} t + \phi')\sin(2\pi f_{Doppl} t + \phi) \rangle = \tfrac{1}{2}\sqrt{I_s I_r} \langle \cos \Delta\phi \rangle \quad (5)$$

As is clear from the above, in the present invention, the modulation frequency and the Doppler frequency shift amount may be set so as to be equal (refer to Formula (5)), or they may be set so as to be different from each other (refer to Formula (4)).

Note that the Doppler frequency shift amount (that is, the movement velocity v of the measured object 1006) that can be handled with the present invention is dependent on the response frequency of the light detecting device 1004. That is, it is necessary for the difference between the modulation frequency and the Doppler frequency shift amount to be less than the response frequency; consequently, the higher the response frequency of the light detecting device 1004 (the shorter the storage time), the wider the range of the Doppler frequency shift amount that can be handled by one modulation frequency, making it possible to handle the movement velocity v over a wider range.

Configuration Example 1

Figure 2:
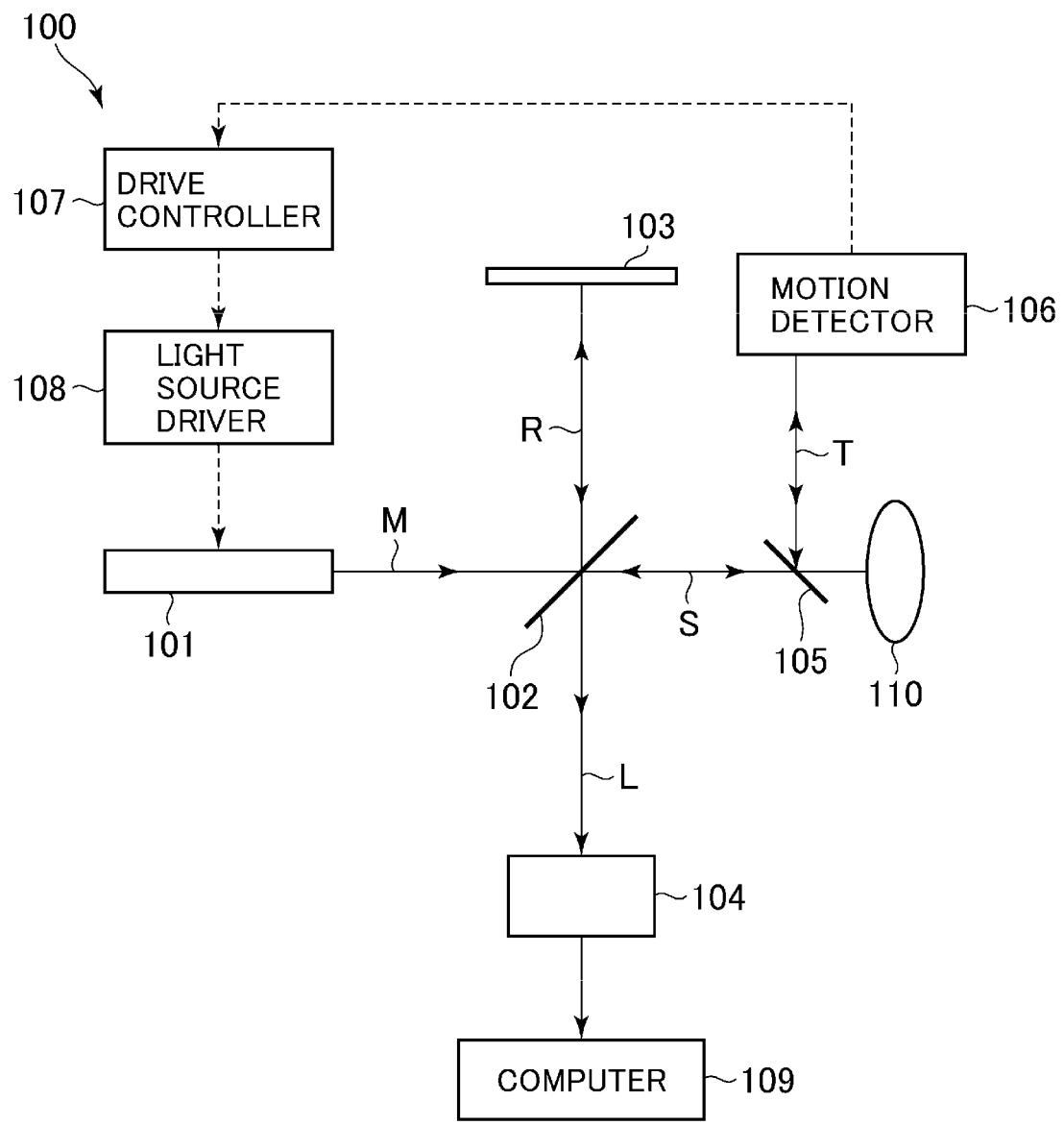
FIG. 2 is a schematic drawing showing an example of the configuration of an embodiment of an optical image measurement apparatus according to the invention.

An explanation is provided regarding a configuration example of an optical image measurement apparatus to which the abovementioned measurement principle is applied. As is the case with conventional apparatuses, the optical image measurement apparatus 100 shown in FIG. 2 divides the output light M from a light source 101 into a signal light S and a reference light R with a beam splitter 102, irradiates a measured object 110 with the signal light S, generates interference light L by superimposing the signal light S passing through the measured object 110 and the reference light R reflected by a reference mirror 103, and detects this interference light L with a light detecting device 104. A computer 109 analyzes this detection result and forms an image of the measured object 110. Moreover, the computer 109 controls each section of the optical image measurement apparatus 100.

A beam splitter 105 is obliquely arranged on the optical path (signal optical path) of the signal light S, that is, between the beam splitter 102 and the measured object 110. The beam splitter 105 irradiates the measured object 110 with light (measurement light) T output from a motion detector 106 along the optical axial direction of the signal light S (that is, in the irradiation direction of the signal light S with respect to the measured object 110). Note that the wavelengths (wavelength range) of the measurement light T and the signal light S (the output light M) may be the same or they may be different.

The measurement light T is reflected by the measured object 110. At this time, if the measured object 110 is moving in the optical axial direction of the signal light S, the frequency (wavelength) of the measurement light T changes, as a result of the Doppler effect. The amount of this change in the frequency is the Doppler frequency shift amount.

The reflected light of the measurement light T from the measured object 110 returns to the motion detector 106 after being reflected by the beam splitter 105. The motion detector 106 receives the reflected light of the measurement light T. As above, information showing the state of motion of the measured object 110 (Doppler frequency shift amount) is included in this reflected light. The motion detector 106 calculates the Doppler frequency shift amount based on the light receiving result of this reflected light, and transmits it to a drive controller 107. Note that the configuration example of the motion detector 106 is described subsequently (refer to FIG. 4 and FIG. 5).

The drive controller 107 controls a light source driver 108 based on the Doppler frequency shift amount received from the motion detector 106. For this, the drive controller 107 calculates the modulation frequency of the intensity of the output light M based on the Doppler frequency shift amount. If the wavelengths of the output light M and the measurement light T are equal, the Doppler frequency shift amount is set to be the modulation frequency, as is. In contrast, if the wavelengths of the output light M and the measurement light T differ, the ratio of the wavelength of the output light M and the wavelength of the measurement light T is multiplied by the Doppler frequency shift amount and this product is set as the modulation frequency. The drive controller 107 generates electrical signals (driving signals) for driving the light source of the calculated modulation frequency and transmits them to the light source driver 108. The driving signals are, for example, rectangular pulses of the modulation frequency.

The light source driver 108 drives the light source 101 based on the driving signals received from the drive controller 107. Accordingly, the light source 101 outputs the output light M in which the intensity is modulated at the modulation frequency. For example, if the modulation frequency is a rectangular pulse, the light source 101 repeatedly turns the output of the output light M on and off at the modulation frequency.

Using this type of output light M, it is possible to set the modulation frequency and the Doppler frequency shift amount to be (almost) equal. Note that there is very little time difference between the measurement time of the Doppler frequency shift amount for calculating the modulation frequency and the measurement time using the calculated modulation frequency; consequently, unless the movement velocity of the measured object 110 does not change drastically between this period, it is possible to obtain the interference signals including the interfering components shown in Formula (4) and Formula (5).

According to this type of optical image measurement apparatus 100, the apparatus is configured such that the state of motion of the measured object 110 is measured and the intensity of the output light M is modulated at the modulation frequency based on this measurement result; thereby, making it possible to cause the modulation frequency to track the Doppler frequency shift amount based on the state of motion of the measured object 110. Accordingly, even if the measured object 110 is moving, it is possible to obtain clear images.

Moreover, by repeating the measurement of the state of motion of the measured object 110, for example, at a predefined time interval, and at the same time, executing the intensity modulation of the output light M in (nearly) real time, it is possible to track the modulation frequency in (nearly) real time, with respect to the state of motion of the measured object 110.

In this configuration example, a computer 250 is an example of the "forming section." Moreover, the motion detector 106, the drive controller 107, and the light source driver 108 are one example of the "modulating section." Moreover, the motion detector 106 is an example of a "measurement section."

Configuration Example 2

Figure 3:
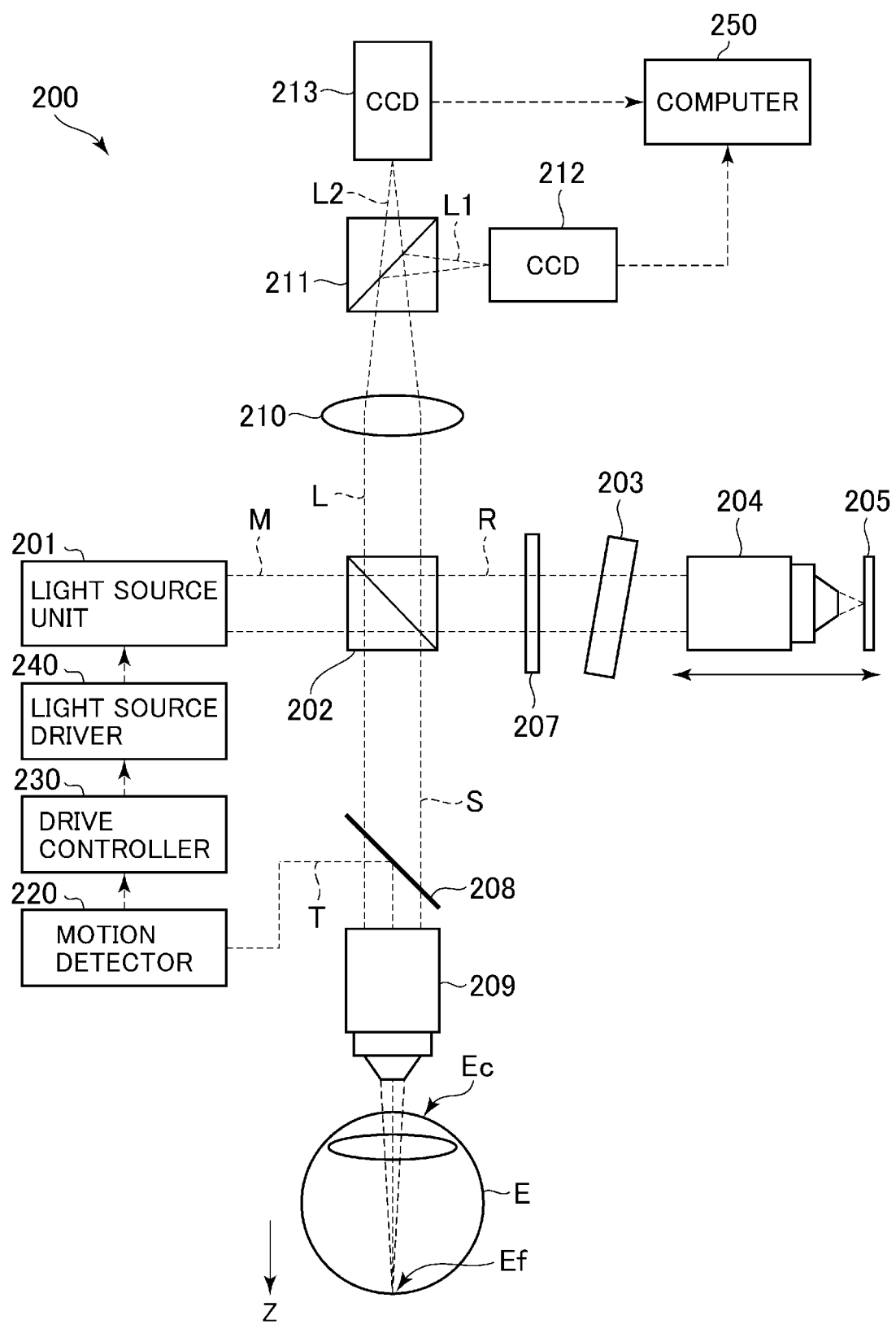
FIG. 3 is a schematic drawing showing an example of the configuration of an embodiment of an optical image measurement apparatus according to the invention.

An explanation is provided regarding a full-field type OCT apparatus (optical image measurement apparatus) in which the measurement principle according to the present invention is applied. A configuration example of this type of optical image measurement apparatus is shown in FIG. 3. This optical image measurement apparatus 200 is an apparatus in which a full-field type OCT apparatus is applied to ophthalmology. A subject's eye E, as a living eye, moves in a complex manner, resulting from pulse beats and accommodative micromovement. The optical image measurement apparatus 200 is used in order to obtain an image of the fundus Ef of the subject's eye E. Note that the optical image measurement apparatus 200 may be configured so as to be able to obtain an image of the cornea Ec.

A light source unit 201, for example, emits output light M of random polarization. Random polarization refers to a polarization state in which two linear polarized components perpendicular to each other exist and the power of each linear polarized component changes temporally in a random manner (for example, refer to Japanese Unexamined Patent Application Publication Hei7-92656).

The light source unit 201 is configured by including light source equipment that emits light of random polarization, an optical fiber bundle that guides this light, a Koehler illumination optical system for uniformly illuminating the irradiation field of the output light, etc. As light source equipment, for example, LEDs (Light Emitting Diodes), SLDs (Super Luminescent Diodes), etc., are used. The light source unit 201 is an example of the "light source" of the present invention.

The output light M from the light source unit 201 is divided into a signal light S and a reference light R by a beam splitter 202.

Moreover, a beam splitter 208 is provided on the optical path (signal optical path) of the signal light S. The beam splitter 208 synthesizes the optical path of the measurement light T from a motion detector 220 to a signal optical path.

Furthermore, an object lens 209 is provided on the signal optical path. The signal light S is focused onto the measuring region of the subject's eye E (the fundus Ef) by the object lens 209. The signal light S is irradiated onto the measuring region with a predetermined beam diameter. At this time, the incident direction of the signal light S with respect to the subject's eye E is in the +z direction (depth direction). The signal light S irradiated onto the subject's eye E is reflected and scattered on the surface and the inner sections of the subject's eye E. This reflected light and scattering light advances in the reverse direction and returns to the beam splitter 202.

A quarter-wave plate wave plate (λ/4 wave plate) 207 and a dispersion compensation member 203 are provided on the optical path (reference optical path) of the reference light R. The reference light R passes through the quarter-wave plate 207 twice. Accordingly, the quarter-wave plate 207 provides an optical path difference equal to one-half the wavelength of the reference light R between the two polarized components (S polarized component, P polarized component) of the reference light R. The dispersion compensation member 203 is constituted from a glass plate having a thickness forming a predetermined optical distance, and it compensates for the dispersion effect that the eyeball optical system of the subject's eye E provides to the signal light S.

Note that in contrast to this embodiment, the quarter-wave plate may be disposed on the signal optical path.

The reference light R passes through the dispersion compensation member 203 and is focused onto the reflection surface of a reference mirror 205 by an object lens 204. The reference light R reflected by the reference mirror 205 passes through the same optical path in the reverse direction and returns to the beam splitter 202.

It is possible to move the reference mirror 205 and the object lens 204 in the propagating direction of the reference light R, resulting from a reference optical path length changing mechanism (not shown in the figures), that is, it is possible to move them in the direction perpendicular to the reflection surface of the reference mirror 205 (the direction of the two-sided arrow in FIG. 3). The reference optical path length changing mechanism is configured by including, for example, actuators such as piezo elements and pulse motors.

Accordingly, the optical path length (the reference optical path length) of the reference light R is changed by moving the reference mirror 205 (and the object lens 204). The reference optical path length is the round-trip distance between the beam splitter 202 and the reference mirror 205. By changing the reference optical path length, it is possible to selectively obtain images of various depth positions of the subject's eye E. That is, this is because interference light L includes, as interfering components, morphological information at the depth position in which the optical path length (the signal optical path length) of the signal light S equals the reference optical path length.

Note that in this embodiment, the reference optical path length is changed; however, it is also possible to configure it such that the signal optical path length is changed. In this case, a mechanism is provided allowing the interval between an apparatus optical system and the subject's eye E to be changed. Examples of this mechanism include stages in which the apparatus optical system is moved in the z direction and stages in which the subject is moved in the z direction. Moreover, this may be configured such that both the reference optical path length and the signal optical path length can be changed.

The signal light S passing through the subject's eye E and the reference light R passing through the reference mirror 205 are superimposed by the beam splitter 202 in order to generate interference light L. The interference light L includes an S polarized component and a P polarized component. A phase difference equal to one-half the wavelength (180°) with each other is provided between these polarized components by the quarter-wave plate 207.

The interference light L generated by the beam splitter 202 is turned into converging light by an imaging lens 210. A polarization beam splitter 211 divides the two polarized components of the interference light L. That is, the S polarized component L1 of the interference light L is reflected on the polarization beam splitter 211 and detected by a CCD (image sensor) 212. In contrast, the P polarized component L2 of the interference light L transmits through the polarization beam splitter 211 and is detected by a CCD (image sensor) 213. The respective CCDs 212, 213 have 2-dimensional light receiving surfaces. The S polarized component L1 and the P polarized component L2 are projected on the light receiving surfaces of the CCD 212, 213, with respective predetermined beam diameters.

The CCD 212 accumulates electric charges by receiving the S polarized component L1 for a predetermined storage time, generates electrical signals (interference signals) based on the accumulated electric charges, and transmits them to the computer 250. Similarly, the CCD 213 accumulates electric charges by receiving the P polarized component L2 for a predetermined storage time, generates electrical signals (interference signals) based on the accumulated electric charges, and transmits them to the computer 250. Electric charge storage times (storage timing) of the CCDs 212, 213 are synchronized. These two interference signals have a phase difference of 180° ($\pi$). The computer 250 forms an image of the subject's eye E based on these interference signals. This image is a tomographical image of the cross-section, which is substantially perpendicular to the optical axial direction (z direction) of the signal light S. Moreover, the computer 250 controls each section of the optical image measurement apparatus 200.

As is the case in the above Configuration Example 1, the optical image measurement apparatus 200 has a motion detector 220, a drive controller 230, and a light source driver 240.

The motion detector 220 measures the state of motion of the subject's eye E in the z direction. The motion detector 220 outputs the measurement light T. The wavelengths (wavelength range) of the measurement light T and the signal light S (output light M) may be the same or they may be different. The measurement light T is irradiated onto the subject's eye E after passing through the beam splitter 208 and the object lens 209. The frequency of the reflected light of the measurement light T from the subject's eye E is changed from the original frequency by the Doppler frequency shift amount corresponding to the movement of the subject's eye E.

The reflected light of the measurement light T from the subject's eye E advances along the same path in the reverse direction and returns to the motion detector 220. The motion detector 220 receives the reflected light of the measurement light T, calculates the Doppler frequency shift amount based on this light receiving result, and transmits it to the drive controller 230.

Figure 4:
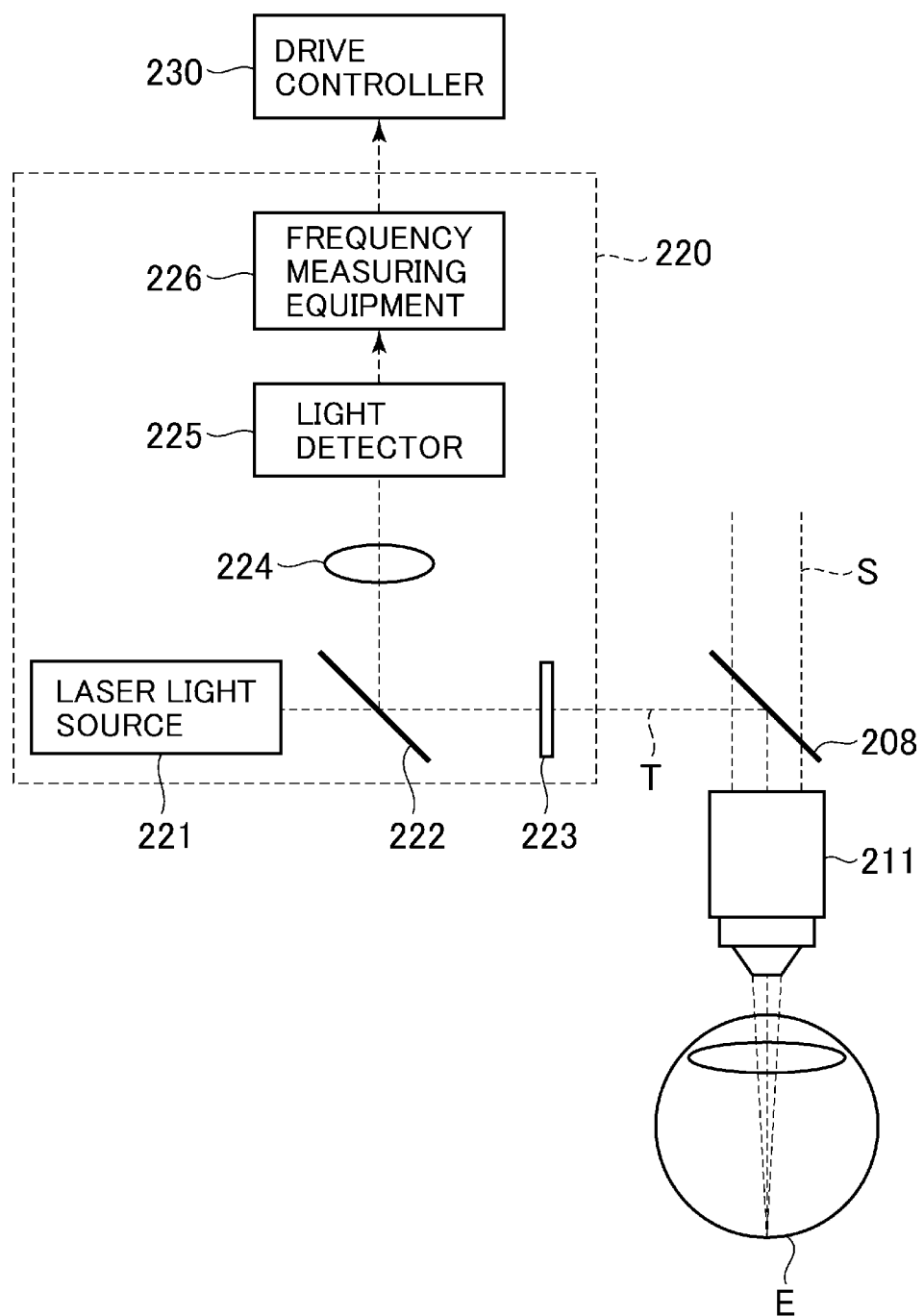
FIG. 4 is a schematic drawing showing an example of the configuration of an embodiment of an optical image measurement apparatus according to the invention.
Figure 5:
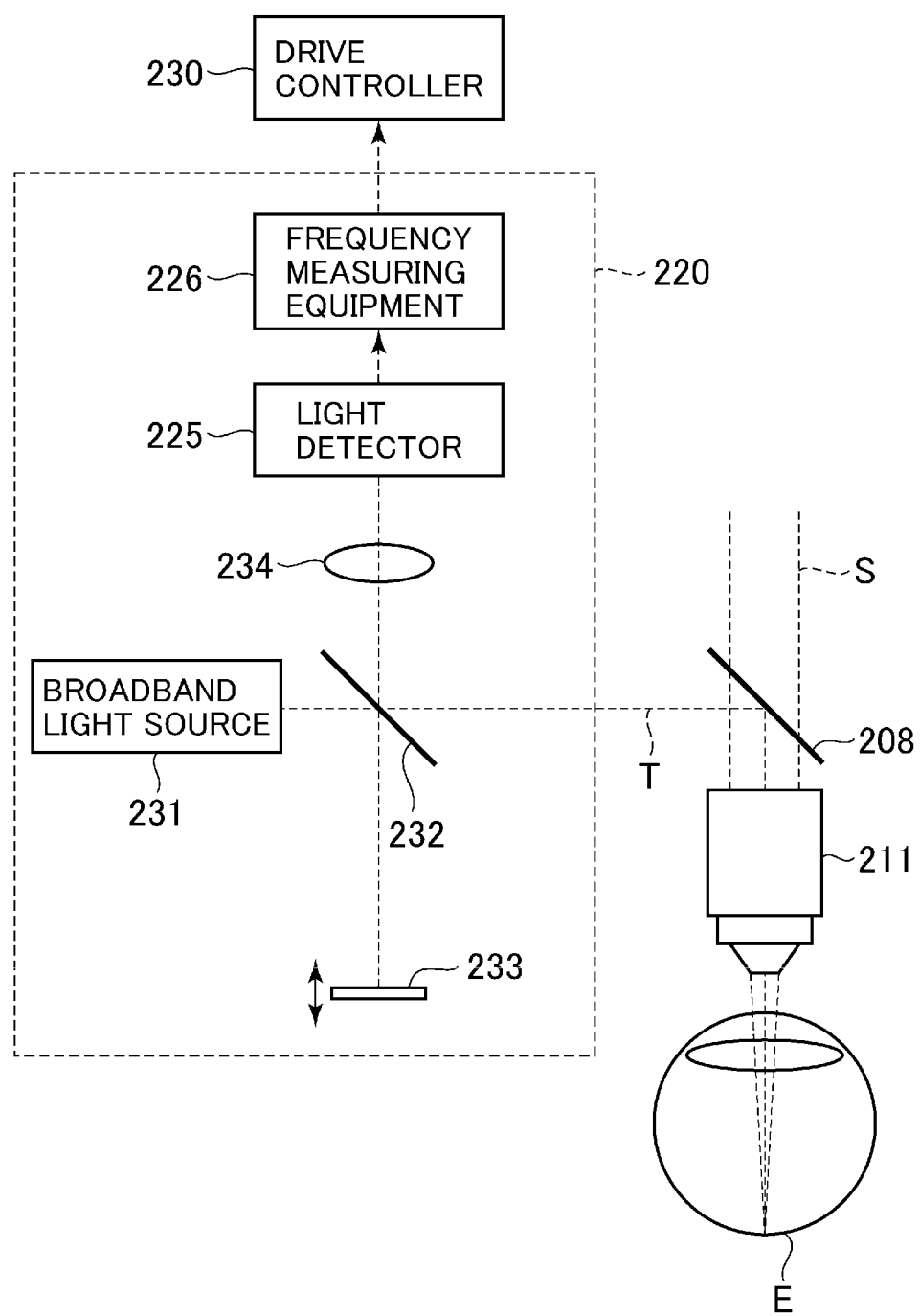
FIG. 5 is a schematic drawing showing an example of the configuration of an embodiment of an optical image measurement apparatus according to the invention.

Here, with reference to FIG. 4 and FIG. 5, two configuration examples of the motion detector 220 are explained. The laser light output from a laser light source 221 of the motion detector 220 shown in FIG. 4 has a relatively long coherence length. The output laser light transmits through a beam splitter 222 and reaches a half-mirror 223. Some of the laser light transmitted through the half-mirror 223 is irradiated on the subject's eye E as the measurement light T.

The reflected light of the measurement light T from the subject's eye E advances along the same path in the reverse direction, reaches the half-mirror 223, and is superimposed with some of the laser light reflected on the half-mirror 223. Accordingly, interference light (measurement interference light) is generated. The measurement interference light is reflected on the beam splitter 222, turns into converging light as a result of an imaging lens 224, and is projected onto the light receiving surface of a light detector 225. Note that it is also possible to configure a confocal optical system by additionally disposing a pinhole and setting the light receiving surface of the light detector 225 to be small.

The light detector 225 generates interference signals based on the detection results of the measurement interference light and transmits them to frequency measuring equipment 226. The frequency measuring equipment 226 calculates the frequency of these interference signals, that is, it calculates the Doppler frequency shift amount, and transmits it to the drive controller 230.

Next, an explanation is provided regarding the motion detector 220 shown in FIG. 5. The broadband light output from a broadband light source 231 of this motion detector 220 is divided into two by a beam splitter 232. The broadband light (standard light) reflected on the beam splitter 232 is reflected by a reflecting mirror 233 and returns to the beam splitter 232. The broadband light transmitted through the beam splitter 232 is irradiated on the subject's eye E as the measurement light T.

The reflected light of the measurement light T from the subject's eye E advances along the same path in the reverse direction, reaches the beam splitter 232, and is superimposed with the standard light. Accordingly, interference light (measurement interference light) is generated. The measurement interference light turns into converging light as a result of an imaging lens 234, and is projected onto the light receiving surface of a light detector 225.

The light detector 225 generates interference signals based on the detection results of the measurement interference light and transmits them to the frequency measuring equipment 226. The frequency measuring equipment 226 calculates frequency of these interference signals, that is, it calculates the Doppler frequency shift amount, and transmits it to the drive controller 230.

It is possible to move the reflecting mirror 233 in the propagating direction of the standard light (in the direction of the two-sided arrow in FIG. 5). Accordingly, the measurement interference light can be generated based on the reflected light of the measurement light T at various depth positions of the subject's eye E, making it advantageous in that it allows not only movement of the entire subject's eye E, but also partial movement of the subject's eye E (for example, micromovement of the fundus Ef) to be selectively measured.

The drive controller 230 calculates the modulation frequency of the intensity of the output light M based on the Doppler frequency shift amount received from the motion detector 220. If the wavelengths of the output light M and the measurement light T are equal, the Doppler frequency shift amount is set as the modulation frequency, as is. If the wavelengths of the output light M and the measurement light T differ, the ratio of the wavelength of the output light M and the wavelength of the measurement light T is multiplied by the Doppler frequency shift amount and this product is set as the modulation frequency. Furthermore, the drive controller 230 generates electrical signals (driving signals) for driving the light source of the calculated modulation frequency and transmits them to the light source driver 240.

The light source driver 240 drives the light source 201 based on the driving signals received from the drive controller 230. Accordingly, the light source 201 outputs the output light M in which the intensity is modulated at the modulation frequency. For example, if the modulation frequency is a rectangular pulse, the light source 201 repeatedly turns the output of the output light M on and off at the modulation frequency.

Using this type of output light M, it is possible to set the modulation frequency and the Doppler frequency shift amount to be (nearly) equal. Accordingly, it is possible to obtain the interference signals including the interfering components shown in Formula (4) and Formula (5).

Figure 6A:
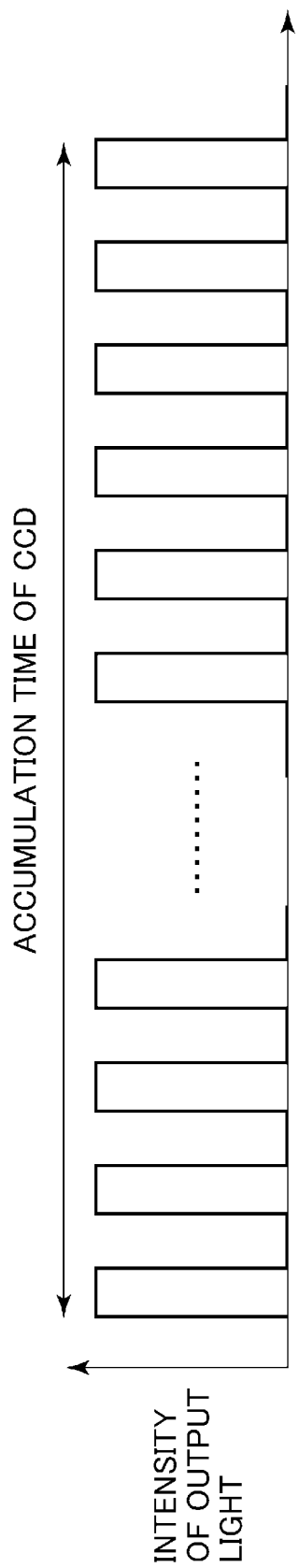
FIG. 6A is a drawing for explaining an example of an interference signal obtained by an embodiment of an optical image measurement apparatus according to the invention.
Figure 6B:
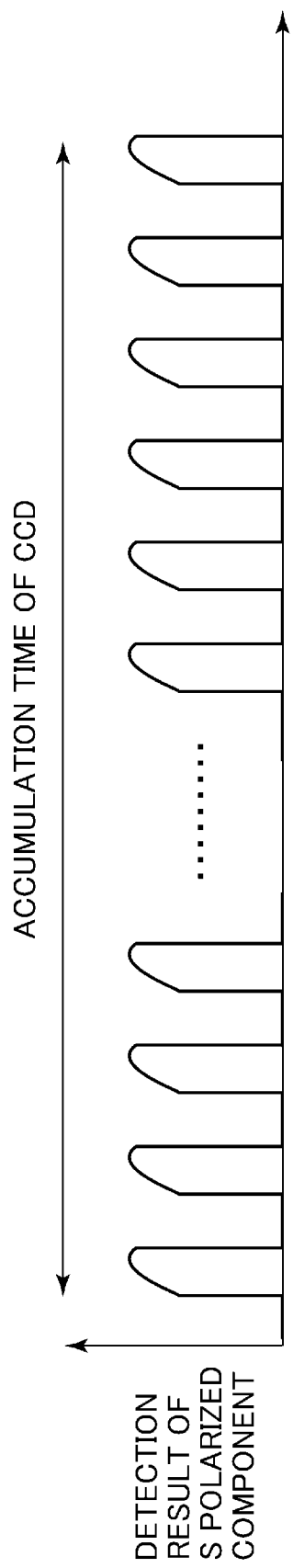
FIG. 6B is a drawing for explaining an example of an interference signal obtained by an embodiment of an optical image measurement apparatus according to the invention.

One example of interference signals that can be obtained by the optical image measurement apparatus 200 is explained based on FIG. 6A to FIG. 6C. FIG. 6A shows the time change in the intensity of the output light M from the light source unit 201. In this example, an explanation is provided for cases in which the light source unit 201 is driven by a rectangular pulse in order to turn the output light M on and off. The output light M is turned on and off at a time interval shorter than the storage time of the respective CCDs 212, 213. In particular, the light source unit 201 is controlled so as to output the output light M a plurality of times within the storage time.

As above, the S polarized component L1 and the P polarized component L2 have a phase difference of 180° ($\pi$). The intensity of a direct-current component of the respective polarized components L1, L2 is $I_s+I_r$. Moreover, the amplitude of the respective polarized components L1, L2 shows a time change in the intensity of an alternating-current component (interfering components). The interfering components of the S polarized component L1 are shown as the second term of Formula (3). The interfering components of the P polarized component L2 have a negative sign (minus) in the second term (or, it may also be expressed by adding $+\pi$ to a phase in the second term).

The CCD 212, as shown in FIG. 6B, continuously detects the S polarized component L1 at the timing in which the output light M is output. Similarly, the CCD 213, as shown in FIG. 6C, continuously detects the P polarized component L2 at a timing in which the output light M is output. Note that the electric charge accumulation timing of the CCDs 212, 213 is synchronized, and the polarized components L1, L2 are respectively detected the same number of times within the storage time. The detection results (interference signals) by the CCDs 212, 213 both have a phase difference of 180°.

The computer 250 forms an image of the subject's eye E by reconstructing a wave shape of the interfering components from these pairs of interference signals.

According to this type of optical image measurement apparatus 200, the apparatus is configured such that the state of motion of the subject's eye E is measured and the intensity of the output light M is modulated at the modulation frequency based on that measurement result; thereby, making it possible to cause the modulation frequency to track the Doppler frequency shift amount based on the state of motion of the subject's eye E and to perform the measurement. Accordingly, even if the subject's eye E is moving resulting from pulse beats, accommodative micromovement, etc., it is possible to obtain clear images.

Moreover, by repeating the measurement of the state of motion of the subject's eye E, for example, at a predefined time interval, and at the same time, executing the intensity modulation of the output light M in (nearly) real time, it is possible to track the modulation frequency in (nearly) real time, with respect to the state of motion of the subject's eye E.

In this configuration example, the light source unit 201 is an example of the "light source." Moreover, the polarization beam splitter 211 is an example of the "division section." Moreover, the CCDs 212, 213 are an example of the "two detectors." Moreover, the computer 250 is an example of the "forming section."

Moreover, the motion detector 220, the drive controller 230, and the light source driver 240 are one example of the "modulating section." Moreover, the motion detector 220 is an example of the "measurement section". Moreover, the laser light source 221 and the broadband light source 231 are examples of the "measurement light source," respectively. Moreover, the beam splitter 222, the half-mirror 223, and the imaging lens 224, shown in FIG. 4, are an example of the "measurement optical system." Moreover, the beam splitter 232, the reflecting mirror 233, and the imaging lens 234, shown in FIG. 5, are an example of the "measurement optical system" and the "measurement interferometer." Moreover, the beam splitter 232 is an example of the "measurement light dividing section." Moreover, the light detector 225 is an example of the "light receiving section."

Configuration Example 3

Figure 7:
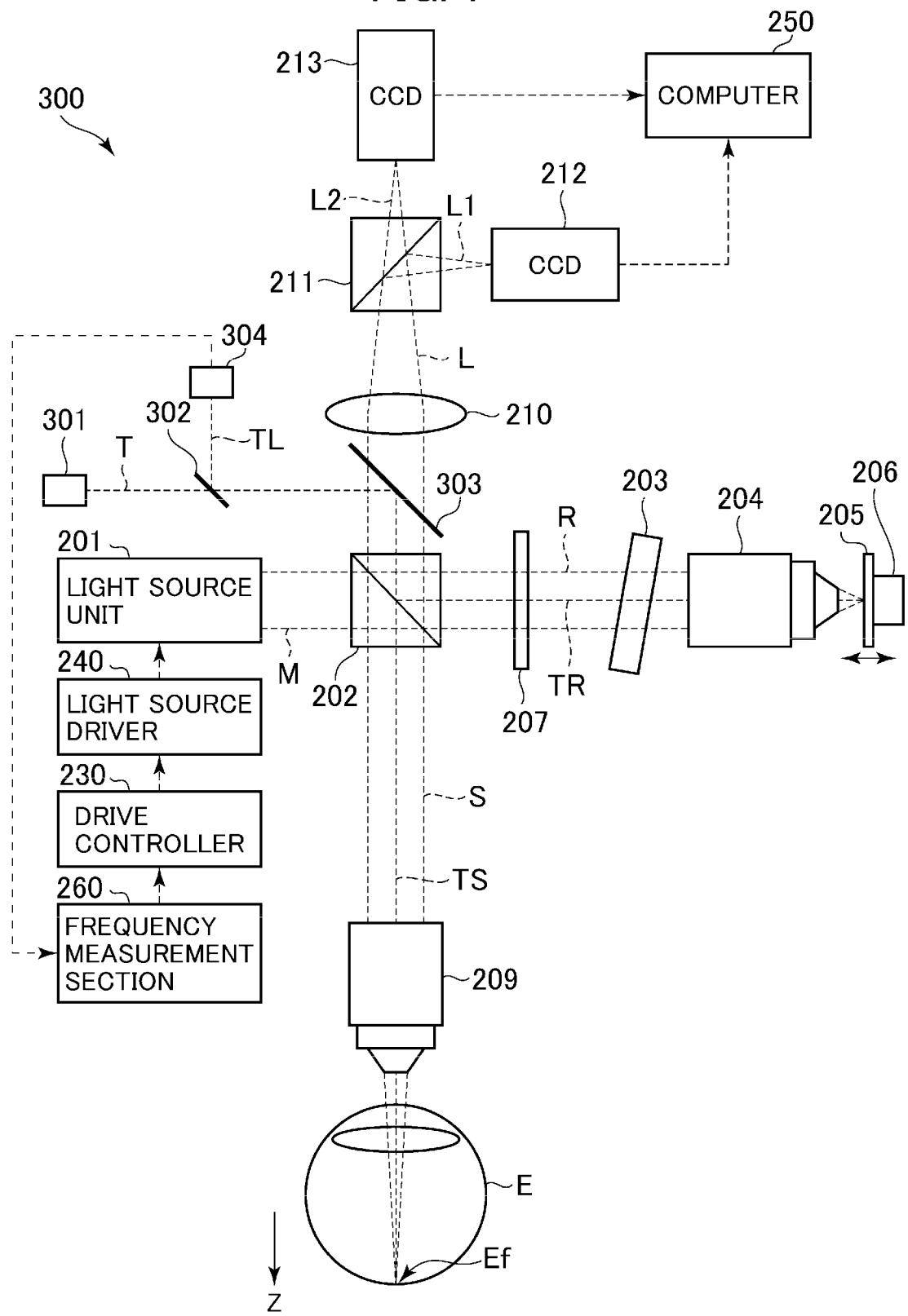
FIG. 7 is a schematic drawing showing an example of the configuration of an embodiment of an optical image measurement apparatus according to the invention.

An explanation is provided regarding another configuration example of the optical image measurement apparatus to which the measurement principle according to the present invention is applied. For the optical image measurement apparatus 300 shown in FIG. 7, a full-field type OCT apparatus is applied to ophthalmology, and the apparatus has nearly the same configuration as that in Configuration Example 2 (refer to FIG. 3). For the configuration sections similar to those in Configuration Example 2, the same symbols are used for explanation purposes. An explanation is provided in more detail below for sections which are different from Configuration Example 2.

The optical image measurement apparatus 300 is not provided with the beam splitter 208 and the motion detector 220 in Configuration Example 2. Instead of these, the optical image measurement apparatus 300 is provided with a measurement light source 301, a beam splitter 302, a dichroic mirror 303, a light detector 304, and a frequency measurement section 260.

Moreover, the optical image measurement apparatus 300 is provided with a reference mirror movement mechanism 206. The reference mirror movement mechanism 206 is configured by including, for example, a piezo element, and moves a reference mirror 205 by a predefined slight distance. This slight distance is set within a coherence length of the output light M. The reference mirror movement mechanism 206 is controlled by the computer 250, and moves the reference mirror 205 so as to change (shift) the frequency of light reflected on the reference mirror 205 (reference light R, measurement light T) by a predetermined frequency.

The measurement light source 301 outputs the measurement light T of a wavelength which is different from that of the output light M. The measurement light source 301 is configured by including, for example, a laser diode. The beam splitter 302 is constituted from, for example, a half-mirror. The dichroic mirror 303 reflects the measurement light T and causes interference light L to transmit through.

The measurement light T output from the measurement light source 301 transmits through the beam splitter 302, is reflected on the dichroic mirror 303, and incident on the beam splitter 202. The beam splitter 202 divides this measurement light T into a first measurement light TS towards the subject's eye E and a second measurement light TR towards the reference mirror 205.

The first measurement light TS is irradiated onto the subject's eye E after passing through an object lens 209. The reflected light of the first measurement light TS from the subject's eye E advances along the same path in the reverse direction and returns to the beam splitter 202. For cases in which the first measurement light TS is reflected on the fundus Ef, if the fundus Ef is moving in the z direction, the frequency of the first measurement light TS is shifted as a result of the Doppler effect.

The second measurement light TR is irradiated onto the reference mirror 205 after passing through a quarter-wave plate 207, a dispersion compensation member 203, and an object lens 204. The reflected light of the second measurement light TR from the reference mirror 205 advances along the same path in the reverse direction and returns to the beam splitter 202. When the light is reflected on the reference mirror 205, the frequency of the second measurement light TR is changed by a predefined frequency.

The beam splitter 202 generates measurement interference light TL by superimposing the first measurement light TS passing through the subject's eye E and the second measurement light TR passing through the reference optical path. The measurement interference light TL based on the first measurement light is reflected on the dichroic mirror 303, and is then reflected on the beam splitter 302 and guided to the light detector 304.

The light detector 304 generates interference signals based on the detection results of the measurement interference light TL, and transmits them to the frequency measurement section 260. As is the case with the frequency measuring equipment 226 in Configuration Example 2, the measurement section 260 calculates the frequency of these interference signals and transmits them to the drive controller 230.

The drive controller 230 calculates the Doppler frequency shift amount resulting from the fundus Ef, based on the frequency of the measurement interference light TL that the frequency measurement section 260 calculated and a predetermined frequency resulting from the reference mirror movement mechanism 206. This Doppler frequency shift amount can be obtained by subtracting the predefined frequency from the frequency of the measurement interference light TL. The drive controller 230 multiplies the ratio of the wavelength of the output light M and the wavelength of the measurement light T by the Doppler frequency shift amount, and sets this product as the modulation frequency. Furthermore, the drive controller 230 generates electrical signals (driving signals) for driving the light source of the calculated modulation frequency and transmits them to the light source driver 240.

The light source driver 240 drives the light source unit 201 based on the driving signals received from the drive controller 230. Accordingly, the light source unit 201 outputs the output light M in which the intensity is modulated at the modulation frequency. Using this type of output light M, it is possible to set the modulation frequency and the Doppler frequency shift amount to be (nearly) equal. Accordingly, it is possible to obtain the interference signals including the interfering components shown in Formula (4) or Formula (5).

According to this type of optical image measurement apparatus 300, the apparatus is configured such that the state of motion of the subject's eye E (the fundus Ef) is measured and the intensity of the output light M is modulated at the modulation frequency based on this measurement result; thereby, making it possible to cause the modulation frequency to track the Doppler frequency shift amount based on the state of motion of the subject's eye E and perform the measurement. Accordingly, even if the fundus Ef is moving as a result of pulse beats, accommodative micromovement, etc., it is possible to obtain clear images.

Moreover, by repeating the measurement of the state of motion of the subject's eye E, for example, at a predefined time interval, and at the same time, executing the intensity modulation of the output light M in (nearly) real time, it is possible to track the modulation frequency in (nearly) real time, with respect to the state of motion of the subject's eye E.

Note that in this configuration example, the optical system including the beam splitter 302, the dichroic mirror 303, and the beam splitter 202 correspond to the "measurement optical system." Moreover, the light detector 304 corresponds to the "light receiving section." Moreover, the reference mirror movement mechanism 206 corresponds to a "change section."

As the configuration for changing the frequency of the light passing through the reference optical path, it is possible to use a 2-dimensional frequency shifter, instead of the reference mirror movement mechanism 206. The 2-dimensional frequency shifter is a device that modulates the frequency of light having a 2-dimensional cross section. Examples of the 2-dimensional frequency shifter include liquid crystal spatial light modulators.

Configuration Example 4

Figure 8:
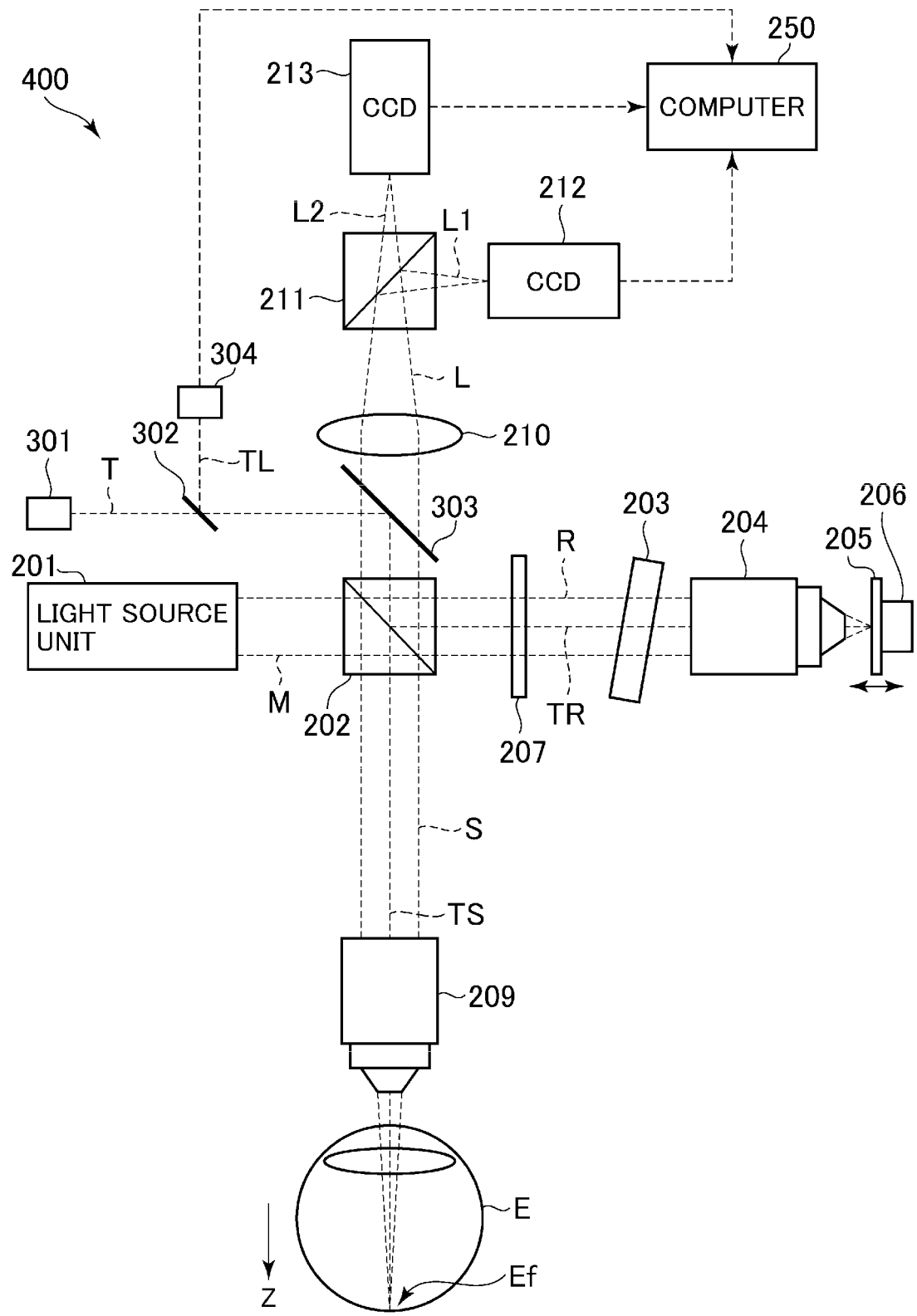
FIG. 8 is a schematic drawing showing an example of the configuration of an embodiment of an optical image measurement apparatus according to the invention.

An explanation is provided regarding another configuration example of the optical image measurement apparatus to which the measurement principle according to the present invention is applied. For the optical image measurement apparatus 400 shown in FIG. 8, a full-field type OCT apparatus is applied to ophthalmology, said apparatus having a similar optical system as that in Configuration Example 3 (refer to FIG. 7). For the configuration sections similar to Configuration Example 3, the same symbols are used for explanation purposes. An explanation is provided in more detail below for sections which are different from Configuration Example 3.

Unlike Configuration Example 3, the optical image measurement apparatus 400 is not provided with the frequency measurement section 260, the drive controller 230, and the light source driver 240. Actions of the light source unit 201 are controlled by the computer 250.

The above configuration example prevents the effect of fringe washout by modulating the intensity of the output light from the light source based on the state of motion of the measured object. In contrast, in this configuration example, the effect of fringe washout is prevented by changing the frequency of the reference light based on the state of motion of the measured object.

The reference mirror movement mechanism 206 is controlled by the computer 250, and changes (shifts) the frequency of light (reference light R, measurement light T) reflected on the reference mirror 205 by moving the reference mirror 205. This frequency shift amount is changed by the computer 250.

Measurement of the state of motion of the fundus Ef using the measurement light T is executed in a similar manner as Configuration Example 3. The light detector 304 generates interference signals based on the detection result of the measurement interference light TL and transmits them to the computer 250. The computer 250, as is the case with the frequency measurement section 260 in Configuration Example 3, calculates the frequency of these interference signals.

Furthermore, the computer 250 calculates the Doppler frequency shift amount resulting from the fundus Ef, based on the frequency of the calculated measurement interference light TL and the change amount (shift amount) of the frequency by the reference mirror movement mechanism 206 at the time of measurement of the state of motion. This Doppler frequency shift amount can be obtained by subtracting the change amount in the above frequency from the frequency of the measurement interference light TL. The computer 250 multiplies the ratio of the wavelength of the output light M and the wavelength of the measurement light T by the Doppler frequency shift amount, and sets this product as the new frequency change amount resulting from the reference mirror movement mechanism 206.

Furthermore, the computer 250 calculates the movement velocity of the reference mirror 205 corresponding to this new change amount, that is, it calculates the movement velocity necessary to change the frequency of light by this new change amount. This processing can be easily carried out by using a formula of the Doppler effect.

The computer 250 controls the reference mirror movement mechanism 206 so as to move the reference mirror 205 at the calculated movement velocity, and at the same time, it controls the light source unit 201 to output the output light M. The frequency of the reference light R based on this output light M is changed by the above new change amount. This new change amount is (nearly) equal to the Doppler frequency shift amount resulting from movement of the fundus Ef. Accordingly, it is possible to obtain the interference signals including the interfering components shown in Formula (4) and Formula (5).

According to this type of optical image measurement apparatus 400, the apparatus is configured such that the state of motion of the fundus Ef is measured and the frequency of the reference light R is changed by the new change amount based on the measurement result; thereby, making it possible to cause the frequency of the reference light R to track the Doppler frequency shift amount based on the state of motion of the fundus Ef and perform the measurement. Accordingly, even if the fundus Ef is moving as a result of pulse beats, accommodative micromovement, etc., it is possible to obtain clear images.

Moreover, by repeating the measurement of the state of motion of the fundus Ef, for example, at a predetermined time interval, and at the same time, changing the frequency of the reference light R in (nearly) real time, it is possible to track the frequency of the reference light R in (nearly) real time, with respect to changes in the state of motion of the fundus Ef.

Note that in this configuration example, the optical system including the beam splitter 302, the dichroic mirror 303, and the beam splitter 202 correspond to the "measurement optical system." Moreover, the light detector 304 corresponds to the "light receiving section." Moreover, the reference mirror movement mechanism 206 corresponds to the "change section."

Note that configuration of the measurement section that measures the state of motion of the fundus Ef is not limited to the above. Moreover, it is also possible to change the frequency of light that passes through the reference optical path, using 2-dimensional frequency shifters such as liquid crystal spatial light modulators.

Modified Example

The configuration explained above is only an example of the optical image measurement apparatus according to the present invention. It is possible for persons attempting to implement the present invention to arbitrarily modify it as long as they stay within the scope of the present invention.

For example, for the motion detector 220 shown in FIG. 5, it is possible to include the interfering components of a predetermined frequency (standard frequency) in the measurement interference light by moving the reflecting mirror 233 at a predetermined speed. The movement velocity of the reflecting mirror 233 is, for example, set such that the standard frequency becomes the frequency at which the intensity modulation frequency of the output light M corresponds to the standard value (standard modulation frequency).

Accordingly, if the subject's eye E is not moving, the intensity of the output light M is modulated at the standard modulation frequency. Moreover, if the subject's eye E is moving, the frequency of the interfering components of the measurement interference light changes from the standard frequency, and the modulation frequency is changed according to this change amount.

According to this modified example, regardless of whether or not the subject's eye E is moving, the intensity of the output light M can be modulated at a suitable modulation frequency, and accordingly, it becomes possible to obtain clear images.

In the above embodiments, the apparatus is configured such that movement of the measured object is measured and the intensity of the output light is modulated based on this measurement result; however, the invention is not limited to this. For example, the apparatus may be configured such that the intensity of light output from the light source is modulated at a frequency (previously set value) corresponding to the movement velocity of the measured object in the irradiation direction of the signal light with respect to the measured object. This modified example is particularly effective for cases in which the measured object moves at a (nearly) constant velocity. That is, the modulation frequency corresponding to this movement velocity may be previously calculated and the intensity of the output light may be modulated at the calculated frequency.

It is possible to configure the apparatus so as to adjust the measurement depth of the measured object, by moving the reference mirror based on the detection results of the state of motion of the measured object. In the above embodiments, the movement velocity of the subject's eye E is measured by detecting the Doppler frequency shift of the reflected light of the measurement light T. If the subject's eye E is moving in the irradiation direction of the measurement light T with respect to the subject's eye E (in the +z direction in FIG. 2), the frequency of reflected light of the measurement light T is lower than the original frequency. In contrast, if the subject's eye E is moving in the −z direction, the frequency of the reflected light of the measurement light T is higher than the original frequency.

Therefore, by providing a means (reflected light measurement section) that receives the reflected light of the measurement light T and measures its frequency and by determining whether or not the measured frequency is higher or lower than the original frequency of the measurement light T, it is possible to obtain the movement direction of the subject's eye E at the time the measurement light T is reflected. Moreover, based on the frequency obtained from the motion detector 220, it is possible to calculate the movement velocity of the subject's eye E. Note that it is also possible to calculate the movement velocity of the subject's eye E by computing the difference between the original frequency and the frequency of the reflected light.

The above reflected light measurement section is, for example, configured as follows. First, on the optical path of the measurement light T, a beam splitter is obliquely arranged to divide the reflected light. Next, the reflected light divided by the beam splitter is received by a light detector. Thereafter, a light receiving result from the light detector is analyzed with the frequency measuring equipment and the frequency of the reflected light is calculated.

This type of measurement is repeatedly carried out at a predefined time interval. By multiplying the movement velocity calculated at each measurement by the measurement interval, a movement distance is obtained for cases in which the subject's eye E is assumed to be moving at a constant velocity within the measurement interval. Note that by setting the measurement interval sufficiently short, the above assumption is nearly satisfied.

By moving the reference mirror 205 by a displacement (movement distance and direction of movement) of the subject's eye E obtained in this way, and changing the optical path length of the reference light R, it is possible to measure nearly the same depth position as after movement. Note that for cases in which a 3-dimensional image of the subject's eye E is obtained while the depth position is sequentially changed, the measurement can be smoothly transferred to the next depth position by adding the movement distance of the reference mirror 205 up to the next depth position to the displacement of the reference mirror 205 based on the above measurement.

Moreover, when measurement is carried out repeatedly, for example, it is possible to calculate a time change in the movement velocity, based on the present measurement result, the last measurement result, and the measurement result before the last measurement, and estimate the movement velocity between the present measurement and next measurement based on this time change. Moreover, by multiplying the estimated value of this movement velocity by the measurement interval, it is possible to obtain a movement distance for cases in which the subject's eye E is assumed to be moving at the estimated value, and it is possible to move the reference mirror 205 by using this movement distance.

In this modified example, the computer 250 computes the displacement of the subject's eye E and moves the reference mirror 205 by this displacement. The computer 250 corresponds to the "optical path length controller" of the present invention. Moreover, the reference optical path length changing mechanism corresponds to the "optical path length change section" of the present invention.

In the above embodiments, the interference light is detected using the CCDs; however, it is possible to use, for example, arbitrary 2-dimensional optical sensor arrays, such as CMOS, instead of the CCDs.

In the above embodiments, the intensity of the output light is modulated by controlling the light source; however, intensity change members, such as shutters or filters, may be provided on the optical path of the output light from the light source that emits continuous light. In this case, the intensity of the output light is modulated by inserting/removing the intensity change member into/from the optical path with respect to the modulation frequency.

In the above embodiments, an explanation was provided regarding the optical image measurement apparatus having a Michelson-type interferometer; however, for example, other interferometers such as a Mach-Zehnder type may also be applied.

Moreover, by providing an optical fiber (bundle) to a section of the interferometer and using it as a light guide member, it is possible to increase the degree of freedom in terms of the device configuration, reduce the size of the device, and increase the degree of freedom in terms of the disposition of the measured object.

The optical image measurement apparatus according to the present invention may arbitrarily combine configurations of the embodiments and/or configuration of the modified example explained above.

EXPLANATION OF THE SYMBOLS 100, 200, 300, 400 Optical image measurement apparatuses
101 Light source
201 Light source unit
103, 205 Reference mirrors
104 Light detecting device
212, 213 CCD's
106, 220 Motion detectors
107, 230 Drive controllers
108, 240 Light source drivers
109, 250 Computers
M Output light
S Signal light
R Reference light
L Interference light
T Measurement light

What is claimed is:

1. An optical image measurement apparatus according comprising:
    an optical system that divides light output from a light source into a signal light and a reference light, irradiates a measured object with said signal light, generates interference light by superimposing said signal light passing through said measured object and said reference light passing through a reference light path, and includes a detecting section that detects the interference light;
    a change section that changes the frequency of light passing through said reference light path;
    a controller that causes said change section to change the frequency based on the movement velocity of said measured object in the irradiation direction of said signal light with respect to said measured object; and
    a forming section that forms an image of said measured object based on the detection results of said interference light generated by said optical system, based on said signal light passing through said measured object and the reference light in which the frequency is changed by said controller,
    wherein a sum of said frequency and a frequency shift amount of said signal light caused by movement of said measured object is higher than a response frequency of said detecting section, and
    wherein said controller includes a measurement section that measures the state of motion of said measured object in said irradiation direction, and causes said change section to change the frequency based on the measurement result.

2. The optical image measurement apparatus according to claim 1, wherein said measurement section includes:
    a measurement light source;
    a measurement optical system that divides the measurement light output from said measurement light source into a first measurement light and a second measurement light, irradiates said measured object with said first measurement light, and generates measurement interference light by superimposing said first measurement light passing through said measured object and said second measurement light passing through said reference light path and in which the frequency is changed by said predetermined frequency; and
    a light receiving section that receives said measurement interference light, and
    said measurement section calculates the frequency of said measurement interference light based on the light receiving results by said light receiving section, and calculates the Doppler frequency shift amount corresponding to the movement velocity of said measured object in said irradiation direction based on the frequency of said measurement interference light and the change amount of the frequency by said change section, as said state of motion, and
    said controller causes said change section to change the frequency by a new change amount based on said Doppler frequency shift amount.

3. The optical image measurement apparatus according to claim 1, wherein
    said optical system includes an optical path length change section that changes the optical path length of said reference light, and comprises an optical path length controller that calculates the displacement of said measured object in said irradiation direction based on said state of motion measured by said measurement section, and changes said optical path length by said displacement by controlling said optical path length change section.

4. The optical image measurement apparatus according to claim 1, wherein
    said optical system includes:
    a quarter-wave plate that is provided on one of the optical paths among said signal light and said reference light and that provides an optical path difference equal to one-half the wavelength between two polarized components of said one light;
    a division section that divides said interference light into said two polarized components; and
    two detectors that detect said two divided polarized components and outputs electrical signals, and
    said forming section forms an image of said measured object based on said two electrical signals based on the two polarized components detected substantially at the same time by said two detectors.

* * * * *